(12) United States Patent
Pehratovic et al.

(10) Patent No.: US 8,613,939 B2
(45) Date of Patent: Dec. 24, 2013

(54) LEAVE-ON NONSOLID SKIN CONDITIONING COMPOSITIONS CONTAINING 12-HYDROXYSTEARIC ACID AND ETHOXYLATED HYDROGENATED CASTOR OIL

(75) Inventors: Hasiba Pehratovic, New Britain, CT (US); Teanoosh Moaddel, Watertown, CT (US); Brian John Dobkowski, Milford, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 255 days.

(21) Appl. No.: 12/968,649

(22) Filed: Dec. 15, 2010

(65) Prior Publication Data

US 2012/0157528 A1 Jun. 21, 2012

(51) Int. Cl.
| | |
|---|---|
| *A61K 8/02* | (2006.01) |
| *C07C 67/08* | (2006.01) |
| *C08K 5/10* | (2006.01) |
| *C08K 5/11* | (2006.01) |
| *C08K 5/00* | (2006.01) |

(52) U.S. Cl.
USPC .......................... 424/401; 524/310; 524/223

(58) Field of Classification Search
USPC ...................................................... 424/401
See application file for complete search history.

(56) References Cited

U.S. PATENT DOCUMENTS

| | | | | |
|---|---|---|---|---|
| 2,862,884 | A | 12/1958 | Dilworth et al. | 252/39 |
| 4,428,885 | A | 1/1984 | Higaki et al. | 260/410.9 |
| 5,380,894 | A | 1/1995 | Burg et al. | 554/219 |
| 5,759,524 | A | 6/1998 | Tanner et al. | 424/59 |
| 6,051,214 | A | 4/2000 | Isbell et al. | 424/70.21 |
| 6,197,343 | B1 | 3/2001 | Minami et al. | 424/489 |
| 6,423,325 | B1 | 7/2002 | Alaluf et al. | 424/401 |
| 6,479,456 | B1 * | 11/2002 | Holzner | 512/1 |
| 6,680,285 | B2 | 1/2004 | Abbas et al. | 510/141 |
| 6,713,051 | B2 | 3/2004 | Mayes et al. | 424/65 |
| 2004/0043044 | A1 | 3/2004 | Granger et al. | 424/401 |
| 2004/0044078 | A1 | 3/2004 | Kawa et al. | 514/558 |
| 2009/0317341 | A1 | 12/2009 | Madison | 424/59 |

FOREIGN PATENT DOCUMENTS

| | | |
|---|---|---|
| EP | 0 129 528 | 12/1984 |
| JP | 56/074197 | 6/1981 |
| JP | 59/227999 | 12/1984 |
| JP | 09/048962 | 2/1997 |
| JP | 4266904 | 5/2009 |
| JP | 2010/138110 | 6/2010 |
| WO | 95/31961 | 11/1995 |
| WO | 2006/056283 | 6/2006 |

OTHER PUBLICATIONS

Co-pending Application: Applicant: Madison, U.S. Appl. No. 12/141,561, filed Jun. 18, 2008.
Co-pending Application: Applicant: Madison, U.S. Appl. No. 12/908,248, filed Oct. 21, 2010.
Co-pending Application: Applicant: Madison et al., U.S. Appl. No. 12/944,289, filed Nov. 11, 2010.
*Analysis Report*, Sree Rayalaseema Alkalies & Allied Chemicals Ltd., Quality Control Laboratory, Jan. 21, 2009.
*Certificate of Analysis*, Vertellus performance Materials, Inc., Jan. 31, 2008.
*Certificate of Analysis*, KIC Chemicals, Inc., Nov. 10, 2009.
*Pelemol® PHS-8*, Phoenix Chemical, Inc., Phoenomenon, Feb. 6, 2007.
Abstract of JP 10 16591—published Jan. 20, 1989.
Abstract of JP 20 13387A—published Jan. 17, 1990.

* cited by examiner

*Primary Examiner* — Layla Soroush
(74) *Attorney, Agent, or Firm* — Rimma Mitelman

(57) ABSTRACT

Leave-on non-solid skin conditioning compositions comprising 12-hydroxy stearic acid. Compositions contain 12HSA, yet have a relatively low viscosity, so are suitable for spreading on the skin, and are stable on storage and structurally reversible through temperature cycling.

8 Claims, No Drawings

LEAVE-ON NONSOLID SKIN CONDITIONING COMPOSITIONS CONTAINING 12-HYDROXYSTEARIC ACID AND ETHOXYLATED HYDROGENATED CASTOR OIL

BACKGROUND OF THE INVENTION

Salts of 12-hydroxystearic acid, i.e. soaps, have been described in wash-off body cleansing compositions (JP 4,266,904; JP 59/227,999, JP 56/074,197). 12-hydroxystearic acid (hereinafter "12HSA") is reported to have a wide variety of beneficial cosmetic effects on skin, e.g. it is a known PPAR-alpha (peroxisome proliferator activated receptors sub-type alpha) activator, skin lightening agent, and a sebum secretion inhibitor. See e.g. Alaluf et al. U.S. Pat. No. 6,423,325, Mayes et al. U.S. Pat. No. 6,713,051, WO2006/056283 (Hindustan Lever), Madison US 2009/0317341, Minami et al. U.S. Pat. No. 6,197,343, Granger et al. US2004/0043044. As such, cosmetic leave-on products containing 12HSA are highly desirable. JP 09-048962 describes the use of 12HSA or its salt as an effective constituent of a solidification inhibitor, to inhibit solidification of a liquid detergent or a liquid cosmetic; all the examples containing a fully neutralized salt of 12HSA. Unfortunately, 12HSA is a solid and has no water solubility and limited oil solubility. Indeed, 12HSA has traditionally been used as gelling agent e.g. in lipsticks and anti-perspirant compositions. See also EP 0129528, U.S. Pat. No. 6,680,285, Abbas et al. U.S. Pat. No. 6,680,285, Tanner et al. U.S. Pat. No. 5,759,524, WO95/31961 (Procter & Gamble), Kawa et al., US 2004/0044078 (describing the use of 12HSA to increase viscosity of cosmetic compositions), and JP 2010/138,110. Salts of 12HSA are only marginally more water-soluble. Thus, non-solid skin conditioning leave-on compositions containing 12HSA are highly desirable.

SUMMARY OF THE INVENTION

The invention includes leave-on non-solid skin conditioning composition comprising:
(a) from about 0.01 to about 15% by weight of the composition of 12-hydroxystearic acid;
(b) from about 0.1 to about 30% by weight of the composition of a nonionic surfactant comprising
  (b1) a high HLB ethoxylated hydrogenated castor oil with an HLB above 10, and
  (b2) a low HLB ethoxylated hydrogenated castor oil with an HLB below 10,
  (b3) wherein the weight ratio of high HLB ethoxylated hydrogenated castor oil to low HLB ethoxylated hydrogenated castor oil is from about 80:20 to about 5:95;
(c) an inorganic neutralizing agent in an amount to maintain the pH of the composition in a range of from about 5.5 to about 8.0;
(d) from about 0.05% to about 10% of a thickening polymer;
(e) wherein the viscosity of the composition is in the range of from about 1 Pas to about 500 Pas,
(f) wherein the composition is structurally reversible through temperature cycling between room temperature and 50° C.

According to the present invention, structurally reversible non-solid skin conditioning compositions have been prepared that contain 12HSA. Structural reversibility of 12HSA containing formulations is crucial, to prevent solidifying of the product on storage, or upon spreading on the skin, rendering it unusable and/or not bioavailable. The invention also includes methods of making and using the compositions.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

"Conditioning" as used herein means prevention and treatment of dry skin, acne, photo-damaged skin, appearance of wrinkles, age spots, aged skin, increasing stratum corneum flexibility, lightening skin color, controlling sebum excretion and generally increasing the quality of skin. The composition may be used to improve skin desquamation and epidermal differentiation and improve skin appearance or general aesthetics.

"Leave-on" as used herein means compositions that are applied to the skin and are not intended to be washed or rinsed off for some period of time, as contrasted with cleansing or wash-off or rinse-off compositions.

"Non-solid" as used herein means that the composition has a measurable viscosity (measurable for instance with a Brookfield Viscometer DV-I+(20 RPM, RV6, 30 Seconds) in the range of from 1 Pas to 500 Pas, preferably from 2 Pas to 100 Pas, more preferably from 3 Pas to 50 Pas.

"Stable" or "Stability" as used herein means that composition does not separate and is not grainy and does not curdle and does not solidify or form a stiff gel.

"Structurally reversible" as used herein means that compositions (i) do not form a stiff gel or solid, do not separate, and do not curdle when initially formulated; and (ii) maintain structural integrity (i.e., the initial appearance and structure) after having been exposed to 50° C. for 24 hours, and then allowed to cool to room temperature. Structural reversibility is gauged by spreading 3-5 grams of a formulation on a dark smooth flat surface (e.g. black lab bench top) and visually observing the film texture. Samples that display structural reversibility have a smooth homogeneous appearance whereas samples that do not display structural reversibility have a grainy surface appearance.

12HSA

The inventive compositions include 12HSA. The compositions typically contain at least 40% of the total 12HSA in its acid form, preferably at least 50%, more preferably at least 60% in order to optimize bioavailability, and therefore efficacy. As with other fatty acids the apparent pKa for 121HSA is expected to be greater than 8. At the pKa, the fatty acid will exist as 50% soap and 50% acid. Therefore, preferably the pH of the inventive compositions is less than about 8, more preferably is in the range of from 5.5 to 8, most preferably is from 6 to 8. 12HSA is included in the inventive compositions in an amount of from 0.01 to 15%, preferably from 0.1 to 12%, more preferably from 0.5 to 10%, and optimally from 1 to 5%. The amounts of 12HSA herein include both acid and salt amounts. The amounts of 12HSA or salts thereof are not meant to be included within the surfactants amounts herein, Ethoxylated Hydrogenated Castor Oil Surfactants It has been found, as part of the present invention, that a specifically tailored mix of nonionic surfactants delivers structurally reversible compositions. Particularly, the nonionic surfactants suitable for use herein result from the condensation reaction of an alkylene oxide and an oil or fatty acid. The preferred nonionic surfactants are of the polyethoxylated castor oil type. Most preferred are the polyethoxylated hydrogenated castor oil type. A mixture of ethoxylated hydrogenated castor oil surfactants is employed, the mixture generally with a minimum HLB of at least about 5, preferably from about 5 to 15. The surfactant compositions are prepared with a mixture of surfactants to allow for versatility and greater stability. The surfactant component generally contains at least one low HLB surfactant having an HLB below 10, preferably below 8 and at least one high HLB surfactant having an HLB above 10, preferably above 12. Particularly preferred from among the high HLB ethoxylated hydrogenated castor oil surfactants is PEG-60 hydrogenated castor oil, Cremophor RH60, and from the low HLB ethoxylated hydrogenated castor oil surfactant is PEG-7 hydrogenated castor oil, Cremophor WO7, both commercially available from BASF. Some other examples of polyethoxylated hydrogenated castor oil surfactants include: Cremophor RH 40 and Cremophor EL. Optionally Cremophors that are not derived from castor oil can also be used, one example, is Cremophor GS 32, polyglyceryl-3 Distearate.

According to the present invention, the ratio of the two ethoxylated hydrogenated castor oil surfactants is important to deliver 12HSA in a predominantly acid form in a non-solid formulation, and to ensure that the formulation is structurally reversible. The ratio of the high HLB ethoxylated hydrogenated castor oil to the low HLB ethoxylated hydrogenated castor oil is in the range from 80:20 to 5:95 more preferably from 70:30 to 10:90, most preferably from 65:35 to 25:75.

Thickening Polymer

The thickening polymer is employed in the present invention, in conjunction, with other elements as described herein, to ensure that the inventive compositions are non-solid and are structurally reversible. 12HSA itself does not deliver a thickening functionality in the inventive compositions.

The thickening polymer is selected from the group consisting of biopolymers, synthetic polymers, and mixtures thereof.

The biopolymer can be chosen, for example, from carrageenan, furcellaran, pectin, alginate, agar, agarose, gellan, glucomannan (e.g., Konjac), galactomannan (e.g., locust bean gum, guar), xanthan, modified cellulose, glucan (e.g., starches, curdlan), gelatin, whey protein or mixtures thereof. More preferably, the biopolymer used is Xanthan gum or modified cellulose. In a most preferred embodiment, the biopolymer used is xanthan gum. The biopolymers suitable for use in this invention are commercially available from suppliers Ashland Aqualon. Additional descriptions of the types of biopolymers that may be used in this invention may be found in Food Gels, Chapter 1, edited by Peter Harris, Elsevier, 1990 and U.S. Pat. Nos. 6,673,371 and 5,738,897, the disclosures of which are incorporated herein by reference.

Illustrative synthetic thickeners (or polymeric viscosity builders) which may also be suitably used include alkylated polyvinylpyrrolidones like butylated polyvinyl pyrrolidone sold under the name Ganex® line by ISP Corporation, terephthalate polyesters like polypropylene terephthalate and ammonium acryloyldimethyltaurate/VP Copolymer, both sold under Aristoflex® line by Clariant A. G.; and mono alkyl esters of poly(methyl vinyl/ether maleic acid) sodium salt, like that included in the EZ Sperse® line made available by ISP Corporation, as well as (3-dimethylaminopropyl)-methacrylamide/3-methacryloylamidopropyl)-lauryl-dimethylammonium chloride like that included in the Styleze® line made available by ISP Corporation. Other thickeners suitable for use include those generally classified as acrylic acid/ethyl acrylate copolymers and carboxyvinyl polymers made available by the B.F. Goodrich Company under the Carbopol name. Such thickeners consist essentially of colloidally water-soluble poly-alkenyl polyether cross-linked polymer of acrylic acid crosslinked with a crosslinking agent like polyallyl sucrose or polyallyl pentaerythritol. These thickeners include, for example, Carbopol 934, 940, 950, 951, 980 and 981.

Other examples of suitable synthetic thickeners for use herein include those sold under the name Carbopol Ultrez 10, Carbopol Ultrez 21, Carbopol ETD2020, Carbopol 1342, Carbopol 1382, and Pemulen TR-1 (CTFA designation: Acrylates/10-30 Alkyl Acrylate Cross-polymer). Other examples of suitable thickeners include those made available by Seppic under the names Sepigel 305 and Sepiplus. Still other examples can include polyurethane alkoxylate polymers from BASF otherwise known as polyurethane-39 sold under the tradename Luvigel STAR. If desired, combinations of synthetic thickeners may be also employed.

Preferably, the thickening polymer is selected from a biopolymer or a synthetic thickener, more preferably from a blend of a biopolymer and a synthetic polymer, optimally a mixture of xanthan gum and taurate polymer (e.g. Aristoflex AVC).

The thickening polymer is included in the inventive compositions in an amount of from 0.05% to 10%, preferably from 0.1 to 8%, more preferably from 0.1 to 5%, optimally from 0.2 to 2%.

Inorganic Neutralizing Agent

Compositions of the present invention include an inorganic neutralizing agent, in order to achieve structural reversibility; it has also been found that when an inorganic neutralizing agent is added, the compositions of the present invention may be produced with a decreased total level of nonionic surfactant. The inorganic neutralizing agent is selected from the group consisting of potassium hydroxide, sodium hydroxide, magnesium chloride, magnesium sulfate, calcium chloride, calcium carbonate, calcium oxide, magnesium oxide, calcium hydroxide, magnesium hydroxide, zinc chloride, zinc oxide, aluminum chloride, aluminum hydroxide, aluminum oxide, and mixtures thereof. Preferably the inorganic neutralizing agent is selected from the group consisting of sodium hydroxide, potassium, hydroxide and zinc oxide. It has been found, as part of the present invention, that an organic neutralizing agent does not provide the desired structural reversibility.

As explained above, the compositions of the present invention contain a substantial, preferably pre-dominant amount of 12HSA in acid form. Therefore, the inorganic neutralizing agent must be used in amount to maintain the preferred pH ranges as discussed above.

Water

The compositions of the present invention are preferably aqueous and include generally from 40 to 99% of water, preferably from 50 to 98%, most preferably from 60 to 97%, optimally from 65 to 95% of water.

Form of the Composition

The compositions of the present invention are non-solid. Essentially, the "non-solidness" of the composition means that the viscosity of the compositions, e.g. as measured using a Brookfield DV-I+viscometer (20 RPM, RV6, 30 seconds). The viscosity is in general is in the range of from 1 Pas to 500 Pas, preferably from 1 Pas to 200 Pas, more preferably from 2 Pas to 100 Pas, most preferably from 3 Pas to 50 Pas.

The compositions of the invention are leave-on compositions. The compositions of the present invention are intended to be applied to remain on the skin. These leave-on compositions are to be distinguished from compositions which are applied to the skin and subsequently removed either by washing, rinsing, wiping, or the like either after or during the application of the product. Surfactants typically used for rinse-off compositions have physico-chemical properties giving them the ability to generate foam/lather in-use with ease of rinse; they can consist of mixtures of anionic, cationic, amphoteric, and nonionic. Surfactants used in leave-on compositions on the other hand are not required to have such properties. Rather, as leave-on compositions are not intended to be rinsed-off they need to be non-irritating and therefore it would be necessary to minimize the total level of surfactant, and particularly the total level of anionic surfactant in leave-on compositions. Therefore, the compositions of the present invention contain, with respect to surfactants, predominantly nonionic surfactants. The anionic surfactants are present in an amount of at most 5%, preferably from 0.01 to 4%, more preferably from 0.01 to 3%, most preferably from 0.01 to 2% and optimally are substantially absent (less than 1%, preferably less than 0.1%, or even less than 0.01%). Salts of 12HSA are not considered anionic surfactants herein. The total level of surfactant in the inventive compositions is preferably no more than 10%, more preferably below 8%, most preferably at most 5%.

The compositions of the present invention are typically in the form of emulsions, which may be oil-in-water, or water-in-oil; preferably the compositions are oil-in-water emulsions. Another preferred format is a cream, furthermore preferably one which has a vanishing cream base. Vanishing cream base is one which comprises 5 to 40% fatty acid and 0.1 to 20% soap. In such creams, the fatty acid is preferably substantially a mixture of stearic acid and palmitic acid and the soap is preferably the potassium salt of the fatty acid mixture, although other counterions and mixtures thereof can be used. The fatty acid in vanishing cream base is often prepared using hystric acid which is substantially (generally about 90 to 95%) a mixture of stearic acid and palmitic acid. A typical hystric acid comprises about 52-55% palmitic acid and 45-48% stearic acid of the total palmitic-stearic mixture. Thus, inclusion of hystric acid and its soap to prepare the vanishing cream base is within the scope of the present invention. It is particularly preferred that the composition comprises higher than 7%, preferably higher than 10%, more preferably higher than 12% fatty acid.

The compositions of the present invention are stable on storage. The compositions remain stable at 45° C. for at least 1 week, more preferably one month, most preferably 3 months, and optimally at least 6 months.

Furthermore, the non-solid leave-on compositions of the present invention are also structurally reversible through temperature cycling between room temperature and 50° C. The inventors found that leave-on formulations containing 12HSA that deliver better have 12HSA in predominantly non-fibrous crystal form in the dry film.

Optional Ingredients
Additional Surfactants

Suitable additional nonionic detergent active compounds can be broadly described as compounds produced by the condensation of alkylene oxide groups, which are hydrophilic in nature, with an organic hydrophobic compound which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

Particular examples include the condensation product of aliphatic alcohols having from 8 to 22 carbon atoms in either straight or branched chain configuration with ethylene oxide, such as a coconut oil ethylene oxide condensate having from 2 to 15 moles of ethylene oxide per mole of coconut alcohol; condensates of alkylphenols whose alkyl group contains from 6 to 12 carbon atoms with 5 to 25 moles of ethylene oxide per mole of alkylphenol; condensates of the reaction product of ethylenediamine and propylene oxide with ethylene oxide, the condensate containing from 40 to 80% of polyoxyethylene radicals by weight and having a molecular weight of from 5,000 to 11,000; tertiary amine oxides of structure $R_3NO$, where one group R is an alkyl group of 8 to 18 carbon atoms and the others are each methyl, ethyl or hydroxyethyl groups, for instance dimethyldodecylamine oxide; tertiary phosphine oxides of structure $R_3PO$, where one group R is an alkyl group of from 10 to 18 carbon atoms, and the others are each alkyl or hydroxyalkyl groups of 1 to 3 carbon atoms, for instance dimethyldodecylphosphine oxide; and dialkyl sulphoxides of structure $R_2SO$ where $R_2$ is an alkyl group, which can be branched of from 10 to 18 carbon, for instance methyl tetradecyl sulphoxide; another example is the condensation product of fatty acid with amines to form $RCONR_1CH_2X$ where R is C8 to C22 (may be branched or ethoxylated), $R_1$ is Hydrogen or methyl, ethyl, $CH_2CH_2OH$; X is $CH_2OH$, $CH_2OR_4$ ($R_4$=ethoxylated i.e CH2CH2OH, CH2CH2OCH2CH2OH).

Further examples of additional nonionic surfactants:
Alkyl Polyglucosides

Alkyl polyglucosides are made from fatty alcohol and sugar. Preferably, the $C_8$-$C_{22}$ or $C_{14}$-$C_{22}$ fatty alcohols forming the fatty unit of the alkyl polyglucosides include a saturated or unsaturated branched or linear alkyl chain respectively containing from 8 to 22 or from 14 to 22 carbon atoms. This includes $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, and $C_{22}$ in any subrange the fatty alcohol is a linear fatty alcohol. Preferably, the fatty unit of the alkyl polyglucosides includes any of decyl, cetyl, behenyl, arachidyl, stearyl, palmityl, myristyl, lauryl, capryl or hexadecanyl units and their mixtures, such as cetearyl (C16-C18 mixture).

Preferable alkylpolyglucosides, such as decylglucoside and laurylglucoside, are sold, for example, by the company Henkel under the respective names Plantaren 2000 and Plantaren 1200, cetostearylglucoside, sold, for example, under the name Tegocare CG90 by the company Goldschmidt and under the name Emulgade KE3302 by the company Henkel. Optionally such surfactants, such as for example cetostearylglucoside, can be sold as a mixture with cetostearyl alcohol, sold, for example, under the name Montanov 68 by the company Seppic, and arachidylglucoside, for example in the form of the mixture of arachidyl and behenyl alcohols and of arachidylglucoside sold under the name Montanov 202 by the company Seppic.

Polyhydroxy Fatty Acid Amides

Polyhydroxy fatty acid amides suitable for use herein are those having the structural formula $R^2CONR^1Z$ wherein: $R^1$ is H, $C_1$-$C_4$, acetyl, 2-hydroxy ethyl, 2-hydroxy propyl, ethoxy, propoxy, or a mixture thereof, preferable $C_1$-$C_4$ alkyl, more preferably $C_1$ or $C_2$ alkyl, most preferably $C_1$ alkyl (i.e., methyl); and $R^2$ is a $C_5$-$C_{31}$, preferably straight-chain $C_5$-$C_{19}$ alkyl or alkenyl, Heteroatom (Oxygen, Nitrogen) containing, branched (alkyl or OH) more preferably straight-chain $C_9$-$C_{17}$ alkyl or alkenyl, most preferably straight-chain $C_{11}$-$C_{17}$ alkyl or alkenyl, or mixture thereof; and Z is a polyhydroxy having a linear hydrocarbon chain with at least 2 hydroxyls directly connected to the chain, or an alkoxylated derivative (preferably ethoxylated or propoxylated) thereof. Z preferably will be derived from carbohydrates; more preferably Z is a glycosyl.

Preferred is a nonionic polyhydroxy fatty acid amide surfactant with $R^2$ from $C_7$ to $C_{16}$, $R^1$ is $C_1$-$C_4$ alkyl, more preferably $C_1$-$C_2$ alkyl, most preferably $C_1$ alkyl i.e. methyl; Z is a polyhydroxy having a linear hydrocarbyl chain with at least two hydroxyls connected to the chain. Most preferred alkyl polyglucosides are selected from the group consisting of hexadecyl polyglucoside, octadecyl polyglucoside, decyl polyglucoside, lauryl polyglucoside, and mixtures thereof.

Sugar Fatty Acid Esters

Esters of fatty acid and sugar include esters or mixtures of esters of linear or branched and saturated or unsaturated $C_{12}$ to $C_{22}$ fatty acids and of sucrose, maltose, glucose, fructose, mannose, galactose, arabinose, xylose, lactose, trehalose or methylglucose. These esters are preferably chosen from mono-, di-, tri- and tetraesters, polyesters and their mixtures. The $C_{12}$ to $C_{22}$ fatty acids includes $C_{12}$, $C_{13}$, $C_{14}$, $C_{15}$, $C_{16}$, $C_{17}$, $C_{18}$, $C_{19}$, $C_{20}$, $C_{21}$, and $C_{22}$ in any subrange or combination. These esters are preferably chosen from stearates, behenates, cocoates, arachidonates, palmitates, myristates, laurates, carprates, oleates, laurates and their mixtures. These compounds can be used in particular as emulsifying surfactants. Mixtures of these derivatives are possible.

Sucrose esters are preferably used. Preferable sucrose esters include sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose polyesters, such as sucrose pentaoleate, hexaoleate, heptaoleate or octooleate, and mixed esters, such as sucrose palmitate/stearate. Mixtures are possible.

Preferable esters or mixtures of esters of fatty acid and of sucrose include those sold by the company Crodesta under the names F160, F140, F110, F90, F70 or SL40, respectively denoting the sucrose palmitate/stearates formed of 73% monoester and 27% di- and triester, of 61% monoester and 39% di-, tri- and tetraester, of 52% monoester and 48% di-, tri- and tetraester, of 45% monoester and 55% di-, tri- and tetraester, of 39% monoester and 61% di-, tri- and tetraester, or sucrose monolaurate. Use may also be made of those sold by the company Mitsubishi under the name Ryoto Sugar esters, for example under the reference B370 corresponding to sucrose behenate formed of 20% monoester and 80% di-, tri- and polyester. Mention may also be made of the sucrose mono- and dipalmitate/stearate sold by the company Goldschmidt under the name "Tegosoft PSE". Use may also be made of a mixture of these various products.

The sugar ester can also be present in admixture with another compound not derived from sugar; and a preferred example includes the mixture of sorbitan stearate and of sucrose cocoate sold under the name "Arlatone 2121" by the company ICI. Other preferable sugar esters include, for example, glucose trioleate, galactose di-, tri-, tetra- or pentaoleate, arabinose di-, tri- or tetralinoleate or xylose di-, tri- or tetralinoleate. Mixtures are possible.

Other preferable esters or mixtures of esters of fatty acid and of methylglucose include the distearate of methylglucose and of polyglycerol-3 sold by the company Goldschmidt under the name of Tegocare 450. Mention may also be made of glucose or maltose monoesters, such as methyl O-hexadecanoyl-6-D-glucoside and (lacuna) O-hexadecanoyl-6-D-maltose.

Other sugar fatty acid ester derivatives which can be used in the composition of the invention include sugar fatty esters which are optionally oxyalkylenated (oxyethylenated and/or oxypropylenated) or polyglycerolated. Preferable oxyethylenated esters of fatty acid and of sugar include oxyethylenated (20 EO) methylglucose sesquistearate, such as the product sold under the name "Glutamate SSE20", by the company Amerchol.

Aldobionamides

Aldobionamides are defined as the amide of an aldobionic acid (or aldobionolactone) and an aldobionic acid is a sugar substance (e.g., any cyclic sugar comprising at least two saccharide units) wherein the aldehyde group (generally found at the $C_1$ position of the sugar) has been replaced by a carboxylic acid, which upon drying cyclizes do an aldonolactone.

An aldobionamide may be based on compounds comprising two saccharide units (e.g., lactobionamides or maltobionamides from the aldobionamide bonds), or they may be based on compounds comprising more than two saccharide units, as long as the terminal sugar in the polysaccharide has an aldehyde group. By definition an aldobionamide must have at least two saccharide units and cannot be linear. Disaccharide compounds such as lactobianomides or maltobionamides are preferred compounds. Other examples of aldobionamides (disaccharides) which may be used include cellobionamides, melibionamides and gentiobionamides.

A specific example of an aldobionamide which maybe used for purposes of the invention is the disaccharide lactobionamide.

Suitable/preferred additional nonionic surfactants include ethoxylated sorbitan fatty acid esters (otherwise known as Tween series from Croda/Uniquema), ethoxylated fatty acids (otherwise known as Brij series from Croda/Uniquema), alternatively other fatty acids can also be optionally added.

Additional Fatty Acids

In a preferred embodiment, compositions of the present invention can further comprise an acid like a fatty acid, in addition to 12HSA. Illustrative non-limiting examples of fatty acids which may be used include saturated or unsaturated branched or linear alkyl chain respectively containing from 8 to 22 or from 14 to 22 carbon atoms. This includes $C_8$, $C_9$, $C_{10}$, $C_{11}$, $C_{12}$, $C_{13}$, $C_{14}$, $C_{15}$, $C_{16}$, $C_{17}$, $C_{18}$, $C_{18:1}$, $C_{18:2}$, $C_{18:3}$, $C_{19}$, $C_{20}$, $C_{21}$, and $C_{22}$.

Anionic Surfactant

Examples of anionic surfactants include sarcosinates, sulfates, isethionates, glycinates, taurates, phosphates, lactylates, glutamates and mixtures thereof. Among isethionates are preferred alkoxyl isethionates such as sodium cocoyl isethionate, sodium lauroyl isethionate and mixtures. Suitable anionic detergent active compounds are water soluble salts of organic sulphuric reaction products having in the molecular structure an alkyl radical containing from 8 to 22 carbon atoms, and a radical chosen from sulphonic acid or sulphuric acid ester radicals, and mixtures thereof. Examples of suitable anionic detergents are sodium and potassium alcohol sulphates, especially those obtained by sulphating the higher alcohols produced by reducing the glycerides of tallow or coconut oil; sodium and potassium alkyl benzene sulphonates such as those in which the alkyl group contains from 9 to 15 carbon atoms; sodium alkyl glyceryl ether sulphates, especially those ethers of the higher alcohols derived from tallow and coconut oil; sodium coconut oil fatty acid monoglyceride sulphates; sodium and potassium salts of sulphuric acid esters of the reaction product of one mole of a higher fatty alcohol and from 1 to 6 moles of ethylene oxide; sodium and potassium salts of alkyl phenol ethylene oxide ether sulphate with from 1 to 8 units of ethylene oxide molecule and in which the alkyl radicals contain from 4 to 14 carbon atoms; the reaction product of fatty acids esterified with isethionic acid and neutralized with sodium hydroxide where, for example, the fatty acids are derived from coconut oil and mixtures thereof.

The preferred water-soluble synthetic anionic detergent active compounds are the alkali metal (such as sodium and potassium) and alkaline earth metal (such as calcium and magnesium) salts of higher alkyl benzene sulphonates and mixtures with olefin sulphonates and higher alkyl sulphates, and the higher fatty acid monoglyceride sulphates.

Other anionic materials useful herein are soaps (i.e., alkali metal salts, e.g., sodium or potassium salts or ammonium or triethanolamine salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.). The fatty acids can also be synthetically prepared. Soaps are described in more detail in U.S. Pat. No. 4,557,853.

Rheology Modifier

A rheology modifier may be included and is selected from the group consisting of silica such as fumed silica or hydrophilic silicas and clays such as magnesium aluminum silicate, betonites, hectorite, laponite, and mixtures thereof. A rheology modifier is employed in an amount of from 0.01 to 2%, preferably from 0.05 to 1%.

Emollients

Emollient materials may serve as cosmetically acceptable carriers. These may be in the form of silicone oils, esters and hydrocarbons. Amounts of the emollients may range anywhere from about 0.1 to about 95%, preferably between about 1 and about 50%, and most preferably from 1-20% by weight of the composition.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 6, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 $m^2/s$ at 25° C. Among the preferred nonvolatile emollients useful in the present compositions are the polydimethyl siloxanes having viscosities from about $1 \times 10^{-5}$ to about $4 \times 10^{-4}$ $m^2/s$ at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:

1) Alkyl esters of saturated fatty acids having 10 to 24 carbon atoms. Examples thereof include behenyl neopentanoate, isopropyl stearate, isopropyl oleate, isononyl isononanoate, isopropyl myristate and octyl stearate and mixtures thereof.

2) Polyhydric alcohol esters. Ethylene glycol mono and di-fatty acid esters, diethylene glycol mono- and di-fatty acid esters, polyethylene glycol (200-6000) di-fatty acid esters, propylene glycol mono- and di-fatty acid esters, polypropylene glycol 2000 monostearate, ethoxylated propylene glycol monostearate, glyceryl di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, are satisfactory polyhydric alcohol esters. Particularly useful are pentaerythritol, trimethylolpropane and neopentyl glycol esters of $C_1$-$C_{30}$ alcohols.

3) Wax esters such as beeswax, spermaceti wax and tribehenin wax.

Hydrocarbons which are suitable cosmetically acceptable carriers include petrolatum, mineral oil, $C_{11}$-$C_{13}$ isoparaffins, and especially isohexadecane, available commercially as Permethyl 101A from Presperse Inc.

Preferred are emollients that can be used, especially for products intended to be applied to the face, to improve sensory properties and are chosen from the group of oils that do not form stiff gels with 12-HSA; these include polypropylene glycol-14 butyl ether otherwise known as Tegosoft PBE, or PPG15 stearyl ether such as Tegosoft E, other oils such as esters, specifically, isopropyl myristate, isopropyl palmitate, other oils could include castor oils and derivatives thereof.

Humectants of the polyhydric alcohol-type can be employed as cosmetically acceptable carriers. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition.

Skin moisturizers, e.g. hyaluronic acid and/or its precursor N-acetyl glucosamine may be included. N-acetyl glucosamine may be found in shark cartilage or shitake mushrooms and are available commercially from Maypro Industries, Inc (New York). Other preferred moisturizing agents include hydroxypropyl tri($C_1$-$C_3$ alkyl)ammonium salts. These salts may be obtained in a variety of synthetic procedures, most particularly by hydrolysis of chlorohydroxypropyl tri($C_1$-$C_3$ alkyl)ammonium salts. A most preferred species is 1,2-dihydroxypropyltrimonium chloride, wherein the $C_1$-$C_3$ alkyl is a methyl group. Amounts of the salt may range from about 0.2 to about 30%, and preferably from about 0.5 to about 20%, optimally from about 1% to about 12% by weight of the topical composition, including all ranges subsumed therein.

Ordinarily the $C_1$-$C_3$ alkyl constituent on the quaternized ammonium group will be methyl, ethyl, n-propyl, isopropyl or hydroxyethyl and mixtures thereof. Particularly preferred is a trimethyl ammonium group known through INCI nomenclature as a "trimonium" group. Any anion can be used in the quat salt. The anion may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate.

Still other preferred moisturizing agents which may be used, especially in conjunction with the aforementioned ammonium salts include substituted urea like hydroxymethyl urea, hydroxyethyl urea, hydroxypropyl urea; bis(hydroxymethyl)urea; bis(hydroxyethyl)urea; bis(hydroxypropyl)urea; N,N'-dihydroxymethyl urea; N,N'-di-hydroxyethyl urea; N,N'-di-hydroxypropyl urea; N,N,N'-tri-hydroxyethyl urea; tetra(hydroxymethyl)urea; tetra(hydroxyethyl)urea; tetra (hydroxypropyl urea; N-methyl, N'-hydroxyethyl urea; N-ethyl-N'-hydroxyethyl urea; N-hydroxypropyl-N'-hydroxyethyl urea and N,N' dimethyl-N-hydroxyethyl urea. Where the term hydroypropyl appears, the meaning is generic for either 3-hydroxy-n-propyl, 2-hydroxy-n-propyl, 3-hydroxy-1-propyl or 2-hydroxy-1-propyl radicals. Most preferred is hydroxyethyl urea. The latter is available as a 50% aqueous liquid from the National Starch & Chemical Division of ICI under the trademark Hydrovance.

Amounts of substituted urea that may be used in the topical composition of this invention range from about 0.01 to about 20%, and preferably, from about 0.5 to about 15%, and most preferably, from about 2 to about 10% based on total weight of the composition and including all ranges subsumed therein.

When ammonium salt and substituted urea are used, in a most especially preferred embodiment at least from about 0.01 to about 25%, and preferably, from about 0.2 to about 20%, and most preferably, from about 1 to about 15% humectant, like glycerine, is used, based on total weight of the topical composition and including all ranges subsumed therein.

Skin Benefit Ingredients

The inventive composition preferably includes an additional skin lightening compound, to obtain optimum skin lightening performance at an optimum cost. Illustrative substances are placental extract, lactic acid, niacinamide, arbutin, kojic acid, ferulic acid, hydroquinone, resorcinol and derivatives including 4-substituted resorcinols and combinations thereof. More preferably, such additional skin lightening compound is a tyrosinase inhibitor, to complement the melanogenesis inhibition activity of the substituted monoamines, most preferably a compound selected from the group consisting of kojic acid, hydroquinone and 4-substituted resorcinol. Also, dicarboxylic acids represented by the formula HOOC—(CxHy)—COOH where x=4 to 20 and y=6 to 40 such as azelaic acid, sebacic acid, oxalic acid, succinic acid, fumaric acid, octadecenedioic acid or their salts or a mixture thereof, most preferably fumaric acid or salt thereof, especially di-sodium salt. It has been found that combination of 12HSA with fumaric acid or salts thereof are particularly preferred, especially for skin lightening formulations. Amounts of these agents may range from about 0.1 to about 10%, preferably from about 0.5 to about 2% by weight of the composition. It is preferred that the skin lightening coactive according to the invention is vitamin B3 or a derivative thereof and is selected from the group consisting of niacinamide, nicotinic acid esters, non-vasodilating esters of nicotinic acid, nicotinyl amino acids, nicotinyl alcohol esters of carboxylic acids, nicotinic acid N-oxide, niacinamide N-oxide and mixtures thereof.

Sunscreen is another preferred ingredient of the inventive compositions. Particularly preferred are such materials as ethylhexyl p-methoxycinnamate (available as Parsol MCX®), Avobenzene (available as Parsol 1789®), octylsalicylate (available as Dermablock OS®), tetraphthalylidene dicamphor sulfonic acid (available as Mexoryl SX®), benzophenone-4 and benzophenone-3 (Oxybenzone). Inorganic sunscreen actives may be employed such as microfine titanium dioxide, zinc oxide, polyethylene and various other polymers. By the term "microfine" is meant particles of average size ranging from about 10 to about 200 nm, preferably from about 20 to about 100 nm. Amounts of the sunscreen agents when present may generally range from 0.1 to 30%, preferably from 2 to 20%, optimally from 4 to 10% by weight of the composition.

More preferred inventive compositions include both the additional skin lightening compound, especially tyrosinase inhibitor, and a sunscreen compound.

Another preferred ingredient of the inventive compositions is a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. Nos. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and U.S. Pat. No. Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof. The retinoid is preferably substantially pure, more preferably essentially pure. The compositions of this invention may contain a safe and effective amount of the retinoid, such that the resultant composition is safe and effective for regulating keratinous tissue condition, preferably for regulating visible and/or tactile discontinuities in skin, more preferably for regulating signs of skin aging, even more preferably for regulating visible and/or tactile discontinuities in skin texture associated with skin aging. The compositions preferably contain from or about 0.005% to or about 2%, more preferably 0.01% to or about 2%, retinoid. Retinol is preferably used in an amount of from or about 0.01% to or about 0.15%; retinal esters are preferably used in an amount of from or about 0.01% to or about 2% (e.g., about 1%); retinoic acids are preferably used in an amount of from or about 0.01% to or about 0.25%; tocopheryl-retinoate, adapalene, and tazarotene are preferably used in an amount of from or about 0.01% to or about 2%.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin B12, Vitamin C, Vitamin D, Vitamin E, Vitamin K and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. A particularly suitable Vitamin $B_6$ derivative is Pyridoxine Palmitate. Flavonoids may also be useful, particularly glucosyl hesperidin, rutin, and soy isoflavones (including genistein, daidzein, equol, and their glucosyl derivatives) and mixtures thereof. Total amount of vitamins or flavonoids when present may range from 0.0001 to 10%, preferably from 0.01% to 1%, optimally from 0.1 to 0.5% by weight of the composition.

Another type of useful substance can be that of an enzyme such as oxidases, proteases, lipases and combinations. Particularly preferred is superoxide dismutase, commercially available as Biocell SOD from the Brooks Company, USA.

Desquamation promoters may be present. Illustrative are the monocarboxylic acids. Monocarboxylic acids may be substituted or unsubstituted with a carbon chain length of up to 16. Particularly preferred carboxylic acids are the alpha-hydroxycarboxylic acids, beta-hydroxycarboxylic or polyhydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic malic and tartaric acids. A representative salt that is particularly preferred is ammonium lactate. Salicylic acid is representative of the beta-hydroxycarboxylic acids. Amounts of these materials when present may range from about 0.01 to about 15% by weight of the composition. Other phenolic acids include ferulic acid, salicylic acid, kojic acid and their salts.

A variety of herbal extracts may optionally be included in compositions of this invention. Illustrative are pomegranate, white birch (*Betula Alba*), green tea, chamomile, licorice and extract combinations thereof. The extracts may either be water soluble or water-insoluble carried in a solvent which respectively is hydrophilic or hydrophobic. Water and ethanol are the preferred extract solvents.

Also included may be such materials as resveratrol, alpha-lipoic acid, ellagic acid, kinetin, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B, Ceramide 6 and Ceramide 7) as well as pseudoceramides may also be utilized for many compositions of the present invention but may also be excluded. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

The compositions of the present invention may contain a safe and effective amount of a peptide active selected from pentapeptides, derivatives of pentapeptides, and mixtures thereof. As used herein, "pentapeptides" refers to both the naturally occurring pentapeptides and synthesized pentapeptides. Also useful herein are naturally occurring and commercially available compositions that contain pentapeptides. A preferred commercially available pentapeptide derivative-containing composition is Matrixyl™, which is commercially available from Sederma, France. The pentapeptides and/or pentapeptide derivative are preferably included in amounts of from about 0.000001% to about 10%, more preferably from about 0.000001% to about 0.1%, even more preferably from about 0.00001% to about 0.01%, by weight of the composition. In embodiments wherein the pentapeptide-containing composition, Matrixyl™, is used, the resulting composition preferably contains from about 0.01% to about 50%, more preferably from about 0.05% to about 20%, and even more preferably from about 0.1% to about 10%, by weight of the resulting composition, of Matrixyl™.

Additional peptides, including but not limited to, di-, tri-, and tetrapeptides and derivatives thereof, and poly amino acid sequences of molecular weight from 200-20000. Amino acids may be naturally occurring or synthetic, dextro or levo, straight chain or cyclized and may be included in the compositions of the present invention in amounts that are safe and effective. As used herein, "peptides" refers to both the naturally occurring peptides and synthesized peptides. Also useful herein are naturally occurring and commercially available compositions that contain peptides.

Suitable dipeptides for use herein include Carnosine. Preferred tripeptides and derivatives thereof may be purchased as Biopeptide CL™, and a copper derivative sold commercially as lamin, from Sigma (St. Louis, Mo.).

Further ingredients useful in skin care compositions herein may be selected from any and all: skin conditioning agents, skin feel mildness agents, suspending agents, auxiliary thickening agents, viscosity control agents, dispersants, solubilizing/clarifying agents, stabilizers, opacifiers/pearlescent agents, chelating/sequestering agents, hydrotropes, bactericides/fungicides, antioxidants, pH control agents, buffering agents, colorants and perfumes/fragrances, water, other optional ingredients (auxiliary agents) and the like.

The compositions of the present invention can also be optionally, incorporated into a water insoluble substrate for application to the skin such as in the form of a treated wipe.

Method of Making Compositions

Compositions within the scope of this invention were prepared in the following manner. Mix all water soluble ingredients including preservatives, thickening polymer, optionally glycerine, and water and heat to a temperature of 70-90° C. In a separate vessel mix all oil soluble ingredients including sugar surfactant and 12HSA to a temperature of 70-90° C.

Add the oil phase to the water phase at a temperature of 70-90° C. with agitation. Optionally, addition of fragrance and phenoxyethanol at 40° C. Cool the mixture to room temperature with mixing.

Method of Using Compositions

The composition according to the invention is intended primarily as a product for topical application to human skin, especially as an agent for conditioning and smoothening the skin, and preventing or reducing the appearance of wrinkled or aged skin, or age spots, or lightening of the skin.

In use, a small quantity of the composition, for example from 1 to 5 ml, is applied to exposed area of the skin, from a suitable container or applicator and, if necessary, it is then spread over and/or rubbed into the skin using the hand or fingers or a suitable device.

While the above summarizes the present invention, it will become apparent to those skilled in the art that modifications, variations and alterations may be made without deviating from the scope and spirit of the present invention as described and claimed herein. The invention will now be further illustrated in the following non-limiting examples.

EXAMPLES

Viscosity measurements were made using Brookfield DV-I+Viscometer (20 rpm, RV6, 30 seconds). HLB values of ethoxylated castor oil surfactants used in the Examples are as follows:

Peg-60 Hydrogenated Castor Oil (Cremophor RH 60) HLB=15-17

Peg-7 Hydrogenated Castor Oil (Cremophor WO 7) HLB=4-6

Example 1

Compositions within the scope of the invention (1-7) and Comparative compositions outside the scope of the invention (A-C) were prepared by adding the oil phase to water phase at 80° C. with agitation. Oil phase and water phase containing polymers were individually heated to 80° C. and then combined at this temperature. Fragrance and phenoxyethanol was added at 40° C. The mixture was then cooled to room temperature with mixing. Comparative Composition A lacked a neutralizing agent. Comparative Composition B lacked a thickening polymer, and Comparative Composition C lacked an ethoxylated castor oil surfactant.

TABLE 1

| | 1 | 2 | 3 | 4 | 5 | 6 | 7 | A | B | C |
| --- | --- | --- | --- | --- | --- | --- | --- | --- | --- | --- |
| | | | | | wt % | | | | | |
| Glycerine | 10 | 10 | 3.5 | 3.5 | 10 | 10 | 10 | 10 | 10 | 10 |
| Hydroxypropyl methyl cellulose | | | | | 1 | 1 | | 1 | | 1 |
| Ammonium polyacryloyldimethyl taurate (Aristoflex AVC) | 0.5 | 0.5 | 0.5 | 0.5 | | | 1 | | | |
| Magnesium aluminum silicate | 0.2 | 0.2 | 0.2 | 0.2 | | | | | | |
| Peg-60 hydrogenated castor oil (Cremophor RH 60) | 2.75 | 2 | 1.65 | 0.47 | 4 | 4 | 4 | 4 | 4 | |
| Polyoxyethylene (20) sorbitan monopalmitate (tween 40) | | | | | | | | | 4 | |
| Peg-7 hydrogenated castor oil (Cremophor WO 7) | 1.75 | 1.3 | 1.10 | 0.32 | 3 | 3 | 3 | 3 | 3 | |
| Sorbitan Stearate (Span 60) | | | | | | | | | | 3 |
| 12-hydroxystearic acid | 3 | 3 | 3 | 3 | 3 | 3 | 3 | 3 | 3 | 3 |
| Dimethicone 200/50 cst | 0.32 | 0.32 | 0.32 | 1 | | | | | | |
| Petrolatum G2212 | 0.25 | 0.25 | 0 | 0 | | | | | | |
| Titanium dioxide | 0.2 | 0.1 | 0.2 | 0.2 | | | | | | |
| Preservatives | 0.7 | 0.7 | 0.7 | 0.7 | 0.7 | 0.7 | 0.7 | 0.7 | 0.7 | 0.7 |
| Disodium EDTA | 0.05 | 0.05 | 0.05 | 0.05 | 0.05 | 0.05 | 0.05 | 0.05 | 0.05 | 0.05 |
| Fragrance | 0.15 | 0.15 | 0.15 | 0.15 | | | | | | |
| Potassium Hydroxide (45%) | | 0.5 | | | | 0.5 | 0.5 | | 0.5 | 0.5 |
| Sodium Hydroxide (50%) | 0.32 | | 0.35 | 0.35 | 0.32 | | | | | |
| Water | to 100 | to 100 | to 100 | to 100 | to 100 | to 100 | to 100 | to 100 | to 100 | to 100 |
| Structural Reversibility | yes | yes | yes | yes | yes | yes | yes | no | no | no |
| Relative ratio high HLB/ low HLB ethoxylated castor oil derivative | 61/39 | 61/39 | 60/40 | 59/41 | 57/43 | 57/43 | 57/43 | 57/43 | 57/43 | — |
| Neutralizing Agent | yes | yes | yes | yes | yes | yes | yes | no | yes | yes |
| Thickening Polymer | yes | yes | yes | yes | yes | yes | yes | yes | no | yes |
| Viscosity (Pas) | 7 | 9.450 | 5.000 | 4.850 | 4.700 | 7.850 | 9.000 | 14.950 | na | 5.700 |
| pH | 7.58 | 7.06 | 7.58 | 7.08 | 8.22 | 7.33 | 7.82 | 5.31 | 6.53 | 6.79 |

It can be seen from the results in Table 1 that compositions within the scope of the invention were structurally reversible, whereas Comparative Compositions A-C were not.

Example 2

Further compositions were prepared as described in Example 1. Composition 8 was within the scope of the invention, Comparative Compositions D-H were outside the scope of the invention.

Composition D contained organic neutralizing agent, instead of inorganic neutralizing agent required by the claims. Composition E contained high HLB ethoxylated castor oil surfactant, but not the low HLB ethoxylated castor oil surfactant. Composition F contained low HLB ethoxylated castor oil surfactant, but not the high HLB ethoxylated castor oil surfactant. Compositions G and H had a ratio of two surfactants outside the claimed range.

TABLE 2

|  | 8 | D | E | F | G | H |
| --- | --- | --- | --- | --- | --- | --- |
|  | wt % | | | | | |
| Glycerine | 10 | 10 | 10 | 10 | 10 | 10 |
| Hydroxypropyl methyl cellulose | 1 | 1 | 1 | 1 | 1 | 1 |
| Peg-60 hydrogenated castor oil (Chremophor RH 60) | 2 | 4 | 7 | 0 | 0.2 | 6.25 |
| Peg-7 hydrogenated castor oil (Chremophor WO 7) | 5 | 3 | 0 | 7 | 6.8 | 0.75 |
| 12-hydroxystearic acid | 3 | 3 | 3 | 3 | 3 | 3 |
| Preservatives | 0.7 | 0.7 | 0.7 | 0.7 | 0.7 | 0.7 |
| Disodium EDTA | 0.05 | 0.05 | 0.05 | 0.05 | 0.05 | 0.05 |
| Potassium Hydroxide (45%) | 0.5 |  | 0.5 | 0.5 | 0.5 | 0.5 |
| TEA (85%) |  | 0.48 |  |  |  |  |
| Water | to 100 | to 100 | to 100 | to 100 | to 100 | to 100 |
| Structural Reversibility | yes | no | no | no | no | no |
| Relative ratio high HLB/low HLB ethoxylated castor oil derivative | 29/71 | 57/43 | 100/0 | 0/100 | 3/97 | 89/11 |
| Neutralizing Agent | yes | yes | yes | yes | yes | yes |
| Thickening Polymer | yes | yes | yes | yes | yes | yes |
| Viscosity (pas) | 4.500 | 12.550 | 2.800 | 9.600 | 8.800 | 3.050 |
| pH | 7.58 | 8.11 | 7.31 | 7.54 | 7.37 | 6.83 |

It can be seen from the results in Table 2 that composition within the scope of the invention (composition 8) was structurally reversible, whereas Comparative Compositions D-H were not.

While described in terms of the presently preferred embodiments, it is to be understood that such disclosure is not to be interpreted as limiting. Various modifications and alterations will no doubt occur to one skilled in the art after having read the above disclosure. Accordingly, it is intended that the appended claims be interpreted as covering all such modifications and alterations as falling within the true spirit and scope of the invention.

What is claimed is:

1. Leave-on non-solid skin conditioning composition comprising:
    (a) from about 0.01 to about 15% by weight of the composition of 12-hydroxystearic acid;
    (b) from about 0.1 to about 30% by weight, of the composition of a nonionic surfactant comprising
        (b1) a high HLB ethoxylated hydrogenated castor oil with an HLB above 10, and
        (b2) a low HLB ethoxylated hydrogenated castor oil with an HLB below 10,
        (b3) wherein the weight ratio of high HLB ethoxylated hydrogenated castor oil to low HLB ethoxylated hydrogenated castor oil is from about 80:20 to about 5:95;
    (c) an inorganic neutralizing agent in an amount to maintain the pH of the composition in a range of from about 5.5 to about 8.0;
    (d) from about 0.05% to about 10% of a thickening polymer;
    (e) wherein the composition is an emulsion or cream and the viscosity of the composition is in the range of from about 1 Pas to about 500 Pas,
    (f) wherein the composition is structurally reversible through temperature cycling between room temperature and 50° C.

2. The composition of claim 1 wherein at least about 40% of 12-hydroxystearic acid is in acid form.

3. The composition of claim 1 wherein the composition remains stable at about 45° C. for at least 1 week.

4. The composition of claim 1 further comprising an anionic surfactant.

5. The composition of claim 1 wherein the inorganic neutralizing agent is selected from the group consisting of potassium hydroxide, sodium hydroxide, magnesium chloride, magnesium sulfate, calcium chloride, calcium carbonate, calcium oxide, magnesium oxide, calcium hydroxide, magnesium hydroxide, zinc chloride, zinc oxide, aluminum chloride, aluminum hydroxide, aluminum oxide, and mixtures thereof.

6. The composition of claim 1 further comprising a fumaric acid or salt thereof.

7. A method of conditioning skin, the method comprising applying to the skin the composition of claim 1.

8. The composition of claim 1 wherein the composition contains from about 60% to about 97% water.

* * * * *